United States Patent
Kim et al.

(10) Patent No.: US 10,881,750 B2
(45) Date of Patent: Jan. 5, 2021

(54) SENTINEL LYMPH NODE MARKER CAPABLE OF MULTI-MODE IMAGING

(75) Inventors: Seok Ki Kim, Goyang-si (KR); Se Hun Kang, Goyang-si (KR); Seo Il Kim, Goyang-si (KR); Young Sang Kim, Goyang-si (KR); Nam Suk Baek, Goyang-si (KR); Jin Hee Noh, Goyang-si (KR)

(73) Assignee: NATIONAL CANCER CENTER, Goyang-si (KR)

( * ) Notice: Subject to any disclaimer, the term of this patent is extended or adjusted under 35 U.S.C. 154(b) by 0 days.

(21) Appl. No.: 13/816,931

(22) PCT Filed: Aug. 16, 2011

(86) PCT No.: PCT/KR2011/005994
§ 371 (c)(1),
(2), (4) Date: Apr. 3, 2013

(87) PCT Pub. No.: WO2012/021045
PCT Pub. Date: Feb. 16, 2012

(65) Prior Publication Data
US 2013/0309169 A1 Nov. 21, 2013

(30) Foreign Application Priority Data
Aug. 13, 2010 (KR) .................. 10-2010-0078330

(51) Int. Cl.
*A61K 51/08* (2006.01)
*A61K 49/00* (2006.01)
*G01N 33/534* (2006.01)

(52) U.S. Cl.
CPC ........ *A61K 51/081* (2013.01); *A61K 49/0002* (2013.01); *A61K 49/006* (2013.01); *A61K 49/0021* (2013.01); *A61K 49/0034* (2013.01); *A61K 49/0056* (2013.01); *G01N 33/534* (2013.01); *G01N 2333/765* (2013.01)

(58) Field of Classification Search
None
See application file for complete search history.

(56) References Cited

FOREIGN PATENT DOCUMENTS

| EP | 1 419 788 A1 | 5/2004 | |
|---|---|---|---|
| EP | 1419787 A1 * | 5/2004 | ......... A61K 49/0093 |
| WO | WO 00/74727 A2 | 12/2000 | |

OTHER PUBLICATIONS

Buckle et al. A self-assembled multimodal complex for combined pre- and intraoperative imaging of the sentinel lymph node. 2010 Nanotechnology 21: 355101. 9 pages. Published online Aug. 6, 2010.*
Kratz F. Albumin as a drug carrier: design of prodrugs, drug conjugates and nanoparticles. 2008 J. Control. Release 132: 171-183.*
Leppälä et al. Accumulation of 99mTc-low-density lipoprotein in human malignant glioma. 1995 Br. J. Cancer 71: 383-387.*
Chin et al. Dual-emissive quantum dots for multispectral intraoperative fluorescence imaging. 2010 Biomaterials 31: 6823-6832. Published online Jun. 18, 2010.*
Hirche et al. ICG fluorescence-guided sentinel node biopsy for axillary nodal staging in breast cancer. 2010 Breast Cancer Res. Treat. 121: 373-378. (Year: 2010).*
Olivier Tiffet et al, Feasibility of the 1, 3, 4, 7, Detection of the Sentinel Lymph Node in Peripheral Non-small Cell Lung Cancer With Radio Isotopic and Blue Dye Techniques, Chest, vol. 127, No. 2, Feb. 1, 2005, pp. 443-448, XP055254664, US.

* cited by examiner

*Primary Examiner* — Jennifer Lamberski
(74) *Attorney, Agent, or Firm* — Sughrue Mion, PLLC (57) ABSTRACT

The present invention relates to a sentinel lymph node marker comprising an albumin; a radioactive isotope and/or near infrared dye which is bound to the albumin; and a visible dye which is bound to the albumin, a preparation method thereof, and a kit for multimode imaging of a sentinel lymph node to prepare the sentinel lymph node marker. The sentinel lymph node marker of the invention remains in the sentinel lymph node for a long period of time and allows for multimode imaging of the sentinel lymph node. Thus, using this marker the sentinel lymph node can be accurately identified in vivo by near infrared imaging and/or gamma imaging without incision of skin, and the location of the identified sentinel lymph node can be precisely identified with the naked eye during a surgical operation of removing the identified sentinel lymph node.

2 Claims, 5 Drawing Sheets

| %ID/g | Brain | Blood | Heart | Lung | Liver | Spleen | Kidney | Sto-mach | Inte-stine | Femur | Muscle | Node | Foot |
|---|---|---|---|---|---|---|---|---|---|---|---|---|---|
| Mouse #1 | 0.01042 | 0.14911 | 0.0731 | 0.13009 | 5.36195 | 3.95606 | 0.97589 | 0.08476 | 0.1437 | 0.34474 | 0.02881 | 15900.5 | 424.679 |
| Mouse #2 | 0.01822 | 0.12247 | 0.09627 | 0.26383 | 7.86045 | 4.57686 | 1.02668 | 0.15288 | 0.13339 | 0.37588 | 0.08101 | 9110.89 | 595.919 |
| Mouse #3 | 0.01581 | 0.18589 | 0.10907 | 0.25807 | 9.03078 | 6.49118 | 1.19905 | 0.11436 | 0.12726 | 0.66921 | 0.10444 | 9474.9 | 377.471 |
| Mean | 0.01482 | 0.15249 | 0.09281 | 0.21733 | 7.41773 | 5.00803 | 1.06721 | 0.11733 | 0.13478 | 0.46328 | 0.07142 | 11495.4 | 466.023 |
| SD | 0.004 | 0.03185 | 0.01823 | 0.0756 | 1.87405 | 1.32142 | 0.11697 | 0.03416 | 0.00831 | 0.17902 | 0.03872 | 3819.22 | 114.942 |

[FIG. 8]

SENTINEL LYMPH NODE MARKER CAPABLE OF MULTI-MODE IMAGING

CROSS REFERENCE TO RELATED APPLICATIONS

This application is the U.S. national phase application of PCT international patent application PCT/KR2011/005994, filed Aug. 16, 2013, which claims priority to Republic of Korea patent application 10-2010-0078330. Each of the aforementioned applications is incorporated herein by reference in its entirety.

BACKGROUND OF THE INVENTION

Field of the Invention

The present invention relates to a sentinel lymph node marker comprising an albumin; a radioactive isotope and/or near infrared dye which is bound to the albumin; and a visible dye which is bound to the albumin, a preparation method thereof, a kit for multimode imaging of a sentinel lymph node to prepare the sentinel lymph node marker, and a method for multimode imaging of a sentinel lymph node using the same.

Description of the Prior Art

As the rate of early detection of tumors increases, a tendency of surgical resection of early cancer has increased. In general, tumor cells tend to infiltrate lymphatic ducts, spread through the lymph to lymph nodes, and metastasize to other organs. Due to this reason, the lymph nodes near a tumor region are often resected in addition to the tumor itself in an early cancer surgery or to prevent metastasis of tumor cells.

However, dissection of lymph node can cause complications such as lymphoedema and drop the quality of patient's living. Thus, it is important to determine the necessity of lymph node dissection for patients and is necessary to reduce the frequency of complications resulting from lymph node dissection significantly by using an appropriate sentinel lymph node marker and sentinel lymph node biopsy. The sentinel lymph node was first targeted by Cabanas et al. in 1977 for treatment of penile cancer and is defined as the first lymph node to receive lymphatic drainage from a primary tumor. Depending on the metastatic status of the sentinel lymph nodes, one can determine whether a distal lymph node after the sentinel lymph node is metastasized or not. If it is found that tumors have not spread to the sentinel lymph node, it can be considered that those tumors have not metastasized to the rest of lymph nodes connected to the sentinel lymph node, thereby avoiding resection of the whole lymph nodes. Thus, a sentinel lymph node biopsy is currently included in standard therapies for treating early breast cancer. Thus, when performing the sentinel lymph node biopsy, a sentinel lymph node marker is critical for identifying the metastasized sentinel lymph node precisely while minimizing the damage to normal tissue by a minimal incision.

In a current practice, a sentinel lymph node is identified by injecting a substance that specifically drains into lymph nodes when injected near to tumor tissue and determining a lymph node where the substance first arrives. Substances with a certain range of particle size (up to several hundred nm) are useful in this method, and various types of particles have been used.

For developing sentinel lymph node markers having the above-described form of particles, various methods have been used using fluorescent and radioactive isotopes. But, the method employing radioactive isotopes is currently used as a standard method.

In addition, low molecular-weight dyes are also used as sentinel lymph node markers. These dyes are visible to the naked eye without the aid of a special imaging system. Some of these dyes have fluorescent properties and thus can be detected relatively easily using a fluorescence imaging system during the operation. Use of dyes only requires a simple apparatus and gives direct information to surgeon. However since the size of dye is too small, its passing time through lymph nodes is extremely short. As a result, the second tier or echelon nodes are stained soon after the sentinel lymph node, making it hard to identify the sentinel lymph node only in the stained tissue. Therefore, the above method using a dye may resect more lymph nodes than necessary and thus has a limitation in minimizing unnecessary incision which is the purpose of targeting sentinel lymph node. Also, a surgical area may be broadly stained, making the operation difficult to perform. In addition, when visible light dyes are used, it is hard to identify the location of the sentinel lymph node by looking at the skin itself without incising it. On the other hand, when fluorescent substance is used, it is easy to identify the location of the sentinel lymph node relative to a conventional visible light dye. However, the location is still hard to identify without incising the skin in case when the wavelength of the fluorescent substance overlaps with that of visible light. But, when a near infrared wavelength fluorescence-emitting substance is used, the location of the sentinel lymph node can be identified without incising the skin.

In the current clinical practice, a radioactive colloid is frequently used, whose passing time through lymph nodes is long enough to mark only the sentinel lymph node for relative long time and that is capable of identifying the marked sentinel lymph node regardless of the depth of skin. However, the above method has shortcomings in that a special apparatus is required and that an operating surgeon cannot perform incision by directly looking at the sentinel lymph node in the operation room. If the whole apparatus is completely equipped, the radioactive colloid is considered as the most accurate and convenient method, but in a practical setting, dyes are often used together with the radioactive colloid in order to maximize the detectability of the sentinel lymph node and accuracy of identifying the same. Furthermore, it is known that when performing a sentinel lymph node biopsy, the use of radioactive colloid along with dyes is the most accurate method for minimizing the false negative results.

However, when both of the radioactive colloid and dyes are administered, several problems arise as follows. First of all, since the passing time of two different substances through lymph nodes is different, the optimal imaging time also differs between two substances. In other words, since the dye passes the lymph nodes extremely fast, when it is used as the sentinel lymph node marker it needs to be injected during the operation. But the radioactive colloid needs to be injected one day or several hours before the operation. As a result, two substances cannot be injected simultaneously by mixing them due to their different properties but rather they need to be injected through two separate injections, incurring a high inconvenience and difficulty in performing.

Secondly, the physical properties of the dyes are unsuitable for labeling the sentinel lymph node. Under the circumstances where no other alternative is available and the use of radioactive substance is not allowed, the dye is also used as a supplemental agent of radioactive colloid. However, the physical properties of the dye does not allow for a specific labeling of the sentinel lymph node, and thus the dye needs to be bound to a substance having a structure capable of remaining in the sentinel lymph node for a longer time if possible. Currently used single-mode detection markers i.e., single-mode detection markers of sentinel lymph node having each of the dyeing, radioactive or fluorescent property cannot individually satisfy all of the ideal properties required to function as a suitable sentinel lymph node marker. Therefore, a suitable agent needs to be developed that can resolve the limitations of the existing sentinel lymph node markers.

Thirdly, since the sentinel lymph node marker is an agent for use in human body, the dye or marker needs to be developed to be suitable for use in human body. Previously developed multimode markers that employ dyes having an excellent luminescent performance and the artificially synthesized nano-sized materials i.e., nanomaterials cannot be used in human body since the in vivo safety thereof has not yet been established.

Fourthly, the properties of dyes need to include a visible light wavelength so that it can be efficiently used by an operating surgeon when resecting lymph nodes. Use of fluorescence or radiation is necessary in the process of identifying the sentinel lymph node, but a marker bound to a visible light dye is also required, since incision of the skin surrounding the identified sentinel lymph node and removal of the sentinel lymph node are performed with the naked eye. However, an agent comprising a sentinel lymph node marker bound to a visible light dye has not been developed yet.

Under given circumstances, in an effort to identify a sentinel lymph node by in vivo imaging without incision of skin, the present inventors have found that when a marker is prepared by binding an albumin with a near infrared dye or labeling it with a radioactive isotope for gamma imaging, and further binding the albumin with a visible dye that allows for a visual identification of a sentinel lymph node during an operation of removing the identified sentinel lymph node, and when the marker comprising the prepared albumin is used, the multimode imaging of the sentinel lymph node becomes possible, thereby completing the present invention.

SUMMARY OF THE INVENTION

An object of the present invention is to provide a sentinel lymph node marker comprising an albumin; a radioactive isotope and/or near infrared dye which is bound to the albumin; and a visible dye which is bound to the albumin.

Another object of the present invention is to provide a method for preparing a sentinel lymph node marker capable of multimode imaging of a sentinel lymph node, which comprises: reducing disulfide bonds of albumin to thiol groups by using a reducing agent to prepare a reduced albumin; labeling the thiol groups of disulfide-reduced form of albumin with a radioactive isotope; and binding the labeled albumin with a visible dye.

Yet another object of the present invention is to provide a kit for multimode imaging of a sentinel lymph node to prepare the above sentinel lymph node marker, the kit comprising: a disulfide-reduced form of albumin; a radioactive isotope and/or near infrared dye; and a visible dye.

Yet another object of the present invention is to provide a method for multimode imaging of a sentinel lymph node, which comprises using the above sentinel lymph node marker.

Effect of the Invention

The sentinel lymph node marker according to the present invention remains in lymph nodes for a long time and thus allows for multimode imaging of a sentinel lymph node. Thus, when this marker is used, the sentinel lymph node can be precisely identified in vivo by near infrared imaging and/or gamma imaging without incision of skin, and the location of the sentinel lymph node can be accurately identified with the naked eye during a surgical operation of removing the identified sentinel lymph node. In addition, the rate of false-negative results occurring can be reduced, the accuracy of a sentinel lymph node biopsy can be increased, and the dependence of the biopsy on apparatus can be reduced. Ultimately, the sentinel lymph node marker of the present invention can be efficiently used in operation for treating breast cancer and melanoma etc. as well as in a sentinel lymph node biopsy for other tumors, or in encoscopy, laparoscopy and robot surgery.

DETAILED DESCRIPTION OF THE INVENTION

In one aspect, the present invention is directed to a sentinel lymph node marker comprising an albumin; a radioactive isotope and/or near infrared dye which is bound to the albumin; and a visible dye which is bound to the albumin.

Albumin that is used in the present invention is a simple protein widely found in the cells or body fluids. It may be a protein that constitutes the basic substance of the cells together with globulin and is widely found in animal and plant tissues. Also, human serum albumin that is used in the present invention may be a protein that has a molecular weight of about 66,462 Da and an isoelectric point (IEP) of about 4.8, and that consists of a single polypeptide chain, constituting about 50% (4 g/) of plasma protein.

When the albumin-containing marker according to the present invention is injected to the interstitial tissue, it can pass through lymphatic ducts and remain specifically in the network structure of lymph nodes without draining into the surrounding capillary vessels. Thus, it remains specifically in the sentinel lymph node (the first lymph node to receive the marker) and shows a high background-to-signal ratio. The human serum albumin in the present invention has a size of 6-8 nm, which is smaller than that of a conventional radioactive colloidal agent so that it can be quickly taken up by the lymph nodes. Also, it is easily accumulated in the sentinel lymph node without passing through the sentinel lymph node, unlike molecular dyes, and thus it passes through lymphatic ducts and remains in lymph nodes without draining into capillary vessels.

Accordingly, the human serum albumin in the present invention is rapidly taken up by the sentinel lymph node and remains in the sentinel lymph node for a long period of time, compared to other colloidal agents. Also, it can be used in human body because it is not toxic.

Previously reported various nanoparticles for multimode imaging are mostly artificially synthesized substances, and thus were mainly tested for in vivo safety in preclinical stages by conducting animal studies. However, the nano-sized human serum albumin that is used in the present invention is a simple protein that is widely found in animal and plant tissues, and it is a marker that may be used in preclinical and clinical applications.

Figure 1:
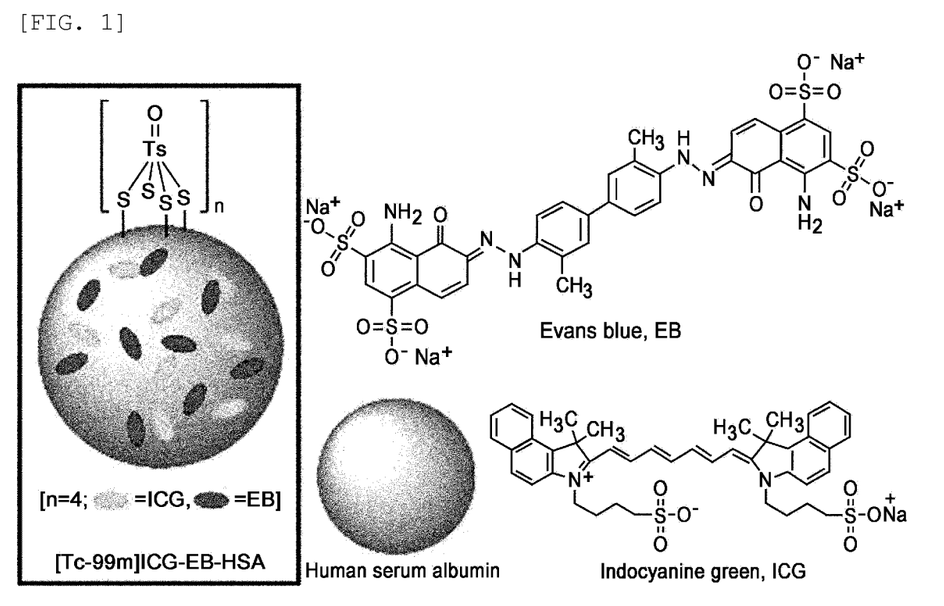
FIG. 1 shows the structure of [Tc-99m]Tc-indocyanine green-Evans blue-human serum albumin.
Figure 2:
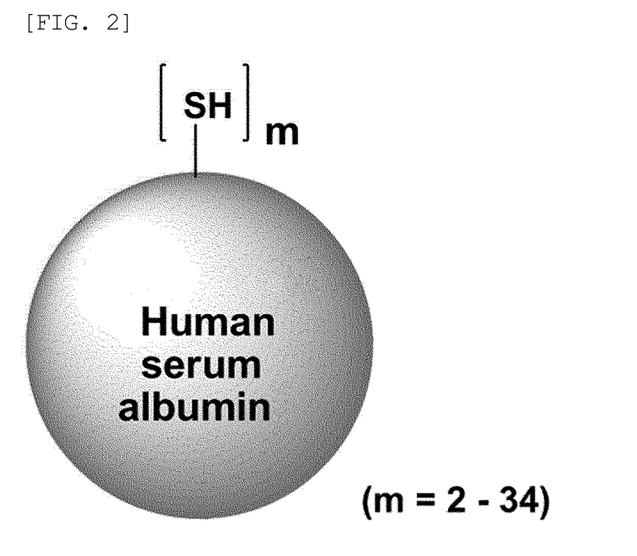
FIG. 2 shows the structure of the disulfide-reduced form of albumin unlabeled with a radioactive isotope.

The human serum albumin in the present invention has 17 disulfide functional groups, and thus when it is reduced with a thiol-containing reducing agent, 2 to 34 thiol groups can be theoretically produced in the human serum albumin (see FIG. 2). In the present invention, the human serum albumin having thiol groups bound thereto, that is, the human serum albumin reduced with thiol groups, is defined as 'the disulfide-reduced form of human serum albumin' or 'thiol human serum albumin'. The thiol groups are moieties that bind to a radioactive isotope and have two or more adjacent thiol groups so as to function as chelates for the radioactive isotope. The radioactive isotope can bind to the thiol groups of human serum albumin, and thus, in one Example of the present invention, [Tc-99m]Tc was used as a radioactive isotope, and the disulfide functional groups of human serum albumin were reduced with a thiol-containing reducing agent to prepare a thiol human serum albumin. As a result an average of 19.1 thiol groups were produced per human serum albumin molecule, and thus the human serum albumin was labeled with up to 4 [Tc-99m]Tc radioactive isotopes. According to one specific embodiment of the present invention, human serum albumin labeled with [Tc-99m]Tc may be represented by the following formula 1:

A-[S—($^{99m}$Tc=O)]$n$              Formula 1 wherein A is the disulfide-reduced form of human serum albumin, S is sulfur, and n is an integer from 1 to 8.

As used herein, the term 'isotope' refers to atoms of the same chemical element that have the same atomic number but differ in atomic mass. Generally, an isotope of any element has the same number of protons and electrons as the element, but has different number of neutrons. Because the chemical properties of an element are determined by the number of protons and electrons thereof, the chemical properties of isotopes thereof are the same as those that element. However, the isotopes differ in the number of neutrons and in mass, and thus can be separated by physical methods. Among isotopes, an isotope having radioactivity is called a radioactive isotope. Since the radioactive isotope radioactively decays by emitting gamma rays or subatomic particles, it is also used as an important marker in diagnosing disease. As a radioactive isotope that may be used as a marker, any radioactive isotope may be used without particular limitation in the present invention, as long as it is known in the art. For example, the radioactive isotope may be $^{131}$I, $^{125}$I, $^{124}$I, $^{64}$Cu, $^{68}$Ga, or $^{99m}$Tc. It is preferably a radioactive isotope that binds to thiol groups, and more preferably, [Tc-99m]Tc. The '[Tc-99m]Tc' is an isotope ($^{99m}$Tc) of technetium (Tc).

When radiation emitted from radioactive isotopes is used, it will have excellent tissue permeability, so that lymph nodes located deep in the body can also be easily identified. Also, it does not cause allergic reactions which may be caused by some of the dyes. Among radioactive isotopes, [Tc-99m]Tc has a low radiation dose and provides high accuracy.

[Tc-99m]TcO$_4^-$ is reduced with a reducing agent such that 4 thiol groups can be coordinated thereto. Thus, a human serum albumin having 2 to 34 thiol groups bound thereto can be theoretically labeled with up to 8 [Tc-99m]Tc atoms. Accordingly, one [Tc-99m]TcO$_4^-$ is bound per 4 thiol groups, and thus n in formula 1 may be an integer from 1 to 8. In one Example of the present invention, the disulfide functional groups of human serum albumin were reduced with a thiol-containing reducing agent to prepare a thiol human serum albumin, and as a result, an average of 19.1 thiol groups per human serum albumin molecule were produced. Thus, as shown in the following formula 2, human serum albumin can be labeled with up to [Tc-99m]Tc atoms.

A-[S—($^{99m}$Tc=O)]$_4$              Formula 2 wherein A is the disulfide-reduced form of human serum albumin, and S is sulfur.

To prepare the sentinel lymph node marker of the present invention, a near infrared dye may be bound to the radioactive isotope-labeled albumin by adsorption, or a near infrared light-absorbing dye may be bound to non-radioactive isotope labeled albumin. As the near infrared dye, any near infrared dye known in the art may be used with limitation in the present invention. Preferably, it may be a near infrared fluorescent dye. More preferably, the near infrared fluorescent dye may be indocyanine green.

As used herein, the term 'near infrared' in the near infrared dye refers to the outer region of the red region of the light spectrum, and the short wavelength region (0.7503 μm) of the infrared region is generally defined as the near infrared region. Near infrared light includes electron spectrums that show thermal, photographic, photoelectric and fluorescent actions and exhibit sterilizing, joint-treating and muscle-treating effects, and thus it is frequently used in industrial and medical applications. The near infrared wavelength region shows relatively light absorption compared to other wavelength regions, and thus near infrared light generated deep in the body can also be externally detected. When near infrared wavelength light is used, there is an advantage in that the location of the sentinel lymph node can be identified without incising the skin.

As used herein, the term 'indocyanine green' refers to a dye for near infrared fluorescence imaging that is widely used. Since it is decomposed or excreted with urine and feces one after injection into the human body, a fluorescent dye can be used in human body and is clinically advantageous.

Coupling the near infrared dye by adsorption can be achieved by mixing the near infrared dye with a radioactive isotope-labeled human serum albumin or a non-radioactive isotope-labeled human serum albumin.

Also, to prepare the sentinel lymph node marker of the present invention, a visible dye can further be bound to the radioactive isotope-labeled albumin or the radioactive isotope-labeled and near infrared dye-bound albumin by adsorption. As the visible dye, any dye that absorbs visible light, known in the art, may be used without limitation. Preferably, the visible dye that is used in the present invention may be Evans blue.

As used herein, the term 'visible' in the visible dye refers to the visible wavelength region of the light spectrum, which generally has a wavelength of 380-770 nm. In the visible wavelength region, the changes in properties according to wavelengths are shown as colors, and wavelengths change progressively from red to violet: 700-610 nm for red; 610-590 nm for orange; 590-570 nm for yellow; 570-500 nm for green; 500-450 nm for blue; and 450-400 nm for violet.

As used herein, the term 'Evans blue' refers to a dye that is used for visual observation in the visible wavelength region. Evans blue allows for detection of a surgical site with the naked eye, is not toxic for use in human body and can be advantageously used in clinical applications.

The near infrared dye and visible dye used in the present invention may be indocyanine green and Evans blue, respectively, which are safe to use in the human body. These dyes are bound to human serum albumin by simple adsorption as opposed to covalent bonding, and thus have no concern about toxicity in clinical use. The use of indocyanine green in human body was reported in several publications, and it was reported that indocyanine green was safe to use in 18 breast cancer patients during clinical trials [T. Kitai, T. Inomoto, M. Miwa, T. Shikayama, Fluorescence navigation with indocyanine green for detecting sentinel lymph nodes in breast cancer, Breast Cancer, 2005, 12, 211-215]. Evans blue has been used as a dye in human body, and a clinical study has been reported showing the results of using Evans blue in 100 breast cancer patients [J.-Y. Bobin, C. Zinzindohoue, S. Isaac, M. Saadat, P. Roy, Eur. J. Cancer, 1999, 35, 569-573].

In one Example of the present invention, the visible dye Evans blue and the near infrared fluorescent dye indocyanine green were bound to [Tc-99m]Tc-labeled human serum albumin by adsorption, thereby preparing an albumin labeled with the radioactive isotope and bound to the near infrared fluorescent dye and the visible dye. In the present invention, unless otherwise specified, '[Tc-99m]Tc-indocyanine green-Evans blue-human serum albumin' refers to an albumin labeled with [Tc-99m]Tc and bound to Evans blue and indocyanine green by adsorption.

The inventive albumin bound to the radioactive isotope and/or near infrared dye, and the visible dye can be used for gamma imaging of the tissue by labeling with the radioactive isotope, for near infrared region (NIR) fluorescence imaging by binding with the near infrared dye, and for visible imaging by binding of the visible dye. Specifically, it enables ex vivo imaging by NIR imaging or gamma imaging without incision of skin, and allows the visual detection of the location of the sentinel lymph node during a surgical operation of removing the identified sentinel lymph node. In other words, inventive albumin where the radioactive isotope and/or near infrared dye, and the visible dye are bound provides multimode imaging, including gamma imaging and/or NIR imaging, and visible imaging.

The gamma image can be observed by various radioactivity detection systems known in the art, and in one Example of the present invention, it was observed using an animal SPECT system (NanoSPECT). In addition, the NIR image can be observed by various NIR image detection systems known in the art, and in one Example of the present invention, the NIR image was observed using a fluorescence imaging system (IVIS Lumina). The visible image could be observed with the naked eye before and after skin incision and was obtained with a digital camera (PowerShot G9) that is commonly used.

The flow of lymph, where the inventive albumin bound to the radioactive isotope and/or near infrared dye, and the visible dye flows into, corresponds to the metastasis of tumor cells from tumor tissue to the surrounding tissue through lymphatic ducts, and the first lymph having the albumin marker that has moved through the lymphatic ducts can be regarded as the first sentinel lymph node where the metastasized tumor cells first spread out.

Thus, after injection of the inventive albumin that is bound to the radioactive isotope and/or near infrared dye, and the visible dye into the body, the albumin flows through lymphatic ducts to lymph nodes and is accumulated in the lymph nodes. Thus, the inventive albumin that is bound to the radioactive isotope and/or near infrared dye, and the visible dye can specifically mark the sentinel lymph node.

The inventive sentinel lymph node marker comprising the albumin that is bound to the radioactive isotope and/or near infrared dye, and the visible dye allows for in vivo imaging of lymph nodes by NIR imaging and/or gamma imaging so that only the skin area around the sentinel lymph node can be incised. In addition, it allows for visual identification of lymph nodes by visible dye. Thus, it leads to a precise and efficient operation. In addition, the present invention allows for multimode imaging of the sentinel lymph node, and thus overcomes all of the limitations in prior art that occur when dyes and radioactive isotopes are individually administered. Thus, the present invention exhibits an excellent effect on labeling of the sentinel lymph node.

In another aspect, the present invention provides a method for preparing a sentinel lymph node marker capable of multimode imaging of a sentinel lymph node, which comprises: reducing disulfide bonds of albumin to thiol groups by using a reducing agent to prepare a reduced albumin; labeling the thiol groups of disulfide-reduced form of albumin with a radioactive isotope; and binding a visible dye with the labeled albumin.

In the method of the present invention, the step of reducing disulfide bonds of albumin to thiol groups by using the thiol-containing reducing agent to prepare a thiol albumin is first carried out.

The reducing agent that is used in the present invention may be a substance that cleaves disulfide bonds of proteins. The thiol group that is used in the present invention is a functional group present in the amino acid cysteine and is involved in an oxidation/reduction reaction in which cysteine is oxidized into cystine. The thiol group is used for the following reasons: when the thiol group is used, [Tc-99m]Tc can be bound to human serum albumin in a simple manner without a synthesis process of attaching chelates (such as MAG3 and Hynic) larger than thiol, so that the change in the structure of the human serum albumin can be minimized, and as a result, the changes in the in vivo physical function of the human serum albumin can also be prevented.

Examples of the thiol-containing reducing agent that is used in the present invention include 2-mercaptoethanol, 1,4-dithiothreitol, 2-aminoethanediol, thioglycolate, cysteine, glutathione, and other compounds known in the art.

Subsequently, the step of labeling the thiol groups of disulfide-reduced form of albumin with a radioactive isotope is carried out. In one Example of the present invention, in order to label the thiol human serum albumin with [Tc-99m]Tc, the disulfide bonds (—S—S—) in the human serum albumin was reduced with the reducing agent, and as a result, it was found that 19.1 thiol (—SH) groups were generated. The thiol group is a functional group that binds to the radioactive isotope [Tc-99m]Tc, and since [Tc-99m]TcO$_4^-$ is reduced such that 4 thiol groups can be coordinated thereto through SnCl$_2$, one albumin molecule can be labeled with up to 4 [Tc-99m]Tc atoms.

Lastly, the step of binding a visible dye with the labeled albumin is carried out. In addition, the method of the present invention may further comprise a step of binding a near infrared dye to the albumin. The binding step is preferably simple binding by adsorption, which does not involve a strong bonding such as covalent bonding, and thus it causes no concern about toxicity in clinical use. Binding of the visible dye and the near infrared dye can be achieved by mixing the visible dye and near infrared dye with the human serum albumin.

Preferably, the near infrared dye may be indocyanine green, and the visible dye may be Evans blue. The visible dye and near infrared dye may be adsorbed to the albumin sequentially or simultaneously.

In still another embodiment, the present invention provides a kit for multimode imaging of a sentinel lymph node to prepare the above sentinel lymph node marker, the kit comprising: a disulfide-reduced form of albumin; a radioactive isotope and/or near infrared dye; and a visible dye.

A method for preparing the kit may comprise the steps of: adding methylene diphosphonic acid, ascorbic acid and stannous chloride to the thiol human serum albumin to prepare a mixture; freeze-drying the mixture; and packaging the dried material in a container. Specifically, the kit can be prepared by adding methylene diphosphonic acid, ascorbic acid and stannous chloride to a dilution of the thiol human serum albumin, adjusting the mixture to a pH of 6, and freeze-drying the mixture at −80° C. for 24 hours, and packaging the dried mixture in a container.

Preferably, the dried material may be packed in a glass bottle. The container is used in order to prepare and store a disposable kit which can be conveniently used by a medical technologist, a medical laboratory technologist or a medical specialist. In one Example of the present invention, a glass bottle was used as the container.

The kit of the present invention may further comprise an antioxidant. The antioxidant serves to prevent the thiol groups of the disulfide-reduced form of human serum albumin from being oxidized to form a polymer. The antioxidant is preferably vitamin C or gentisic acid and is contained in the kit of the present invention in an amount of 500 mg per unit dosage.

The kit is frozen or freeze-dried in a sterile container an inert gas atmosphere. Preferably, it is freeze-stored in liquid nitrogen and can be thawed slowly pr or to use. In order to prepare an in ectable agent which is to be used by a medical technologist, a medical laboratory technologist or a medical specialist, the kit may equipped with buffer, a sterile vial, saline, a syringe, a filter, a column and other auxiliary devices. It is well known to those skilled in the art that the kit can be changed and modified depending on patient's needs or dietary regimes and can be changed such that a radioactive isotope can be provided or obtained.

The kit of the present invention is to be used in the clinical practice of using the sentinel lymph node marker and is designed such that mistakes in using and contamination can be minimized, even in a busy environment of clinical operations, and can be used in an user-friendly manner. In conventional cases, a process of labeling a marker with a radioactive isotope is required before the use of the marker, and since the radioactive isotope has a short half-life, the marker should be labeled with the isotope immediately before its use. For this reason, the present invention provides the above-described kit for a rapid and easy use of the marker with the isotope, facilitating the clinical use of the marker. Using this kit even those non-skilled persons can perform isotope labeling without the aid of a special synthesizing system.

Figure 5:
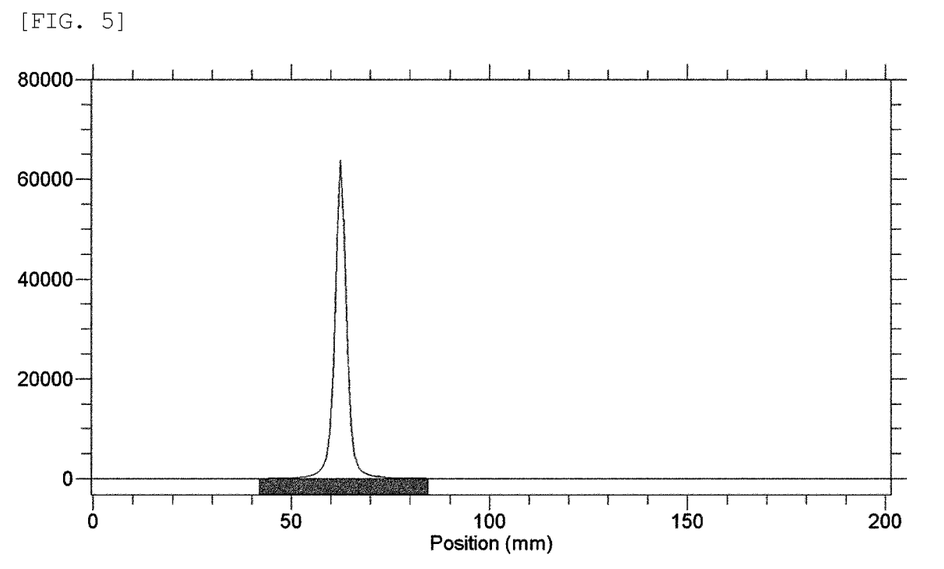
FIG. 5 shows the results of instant thin layer chromatography (ITLC) conducted to confirm the synthesis of [Tc-99m]Tc-human serum albumin. The ITLC was performed using ethanol: 10% acetic acid ammonium=1:1 as a developing solvent, and the labeling ratio was found to be >99%.

In one embodiment of the present invention, the radioactive isotope-labeled human serum albumin represented by Formula 1 can be prepared by adding a radioactive isotope to the kit. In one Example of the present invention, a [Tc-99m]Tc-labeled human serum albumin was synthesized by adding 20 mCi/2 mL of [Tc-99m]TcO$_4^-$ to the thiol human serum albumin kit and allowing the mixture to react at room temperature. The results of the above synthesis reaction could be confirmed by instant thin layer chromatography (ITLC) using ethanol: 10% ammonium acetate=1:1 as a developing solvent, and the labeling ratio was found to be >99%, suggesting that when the disposable kit of the thiol human serum albumin according to the present invention is used, labeling with [Tc-99m]Tc can be successfully done (FIG. 5).

Meanwhile, a human serum albumin labeled with a radioactive isotope and bind to a near infrared fluorescent dye and visible dye could be obtained by adding the near infrared fluorescent dye and visible dye to the radioactive isotope-labeled albumin, mixing the components for binding to each other by adsorption, and purifying the mixture.

In another aspect, the present invention is directed to a method for multimode imaging of a sentinel lymph node, which comprises using the above-described sentinel lymph node marker.

As used herein, the term 'multimode imaging' refers to visualizing the image of a sentinel lymph node by various methods. The sentinel lymph node marker and kit of the present invention can be imaged by gamma imaging and/or near infrared region imaging, and visible imaging.

Figure 8:
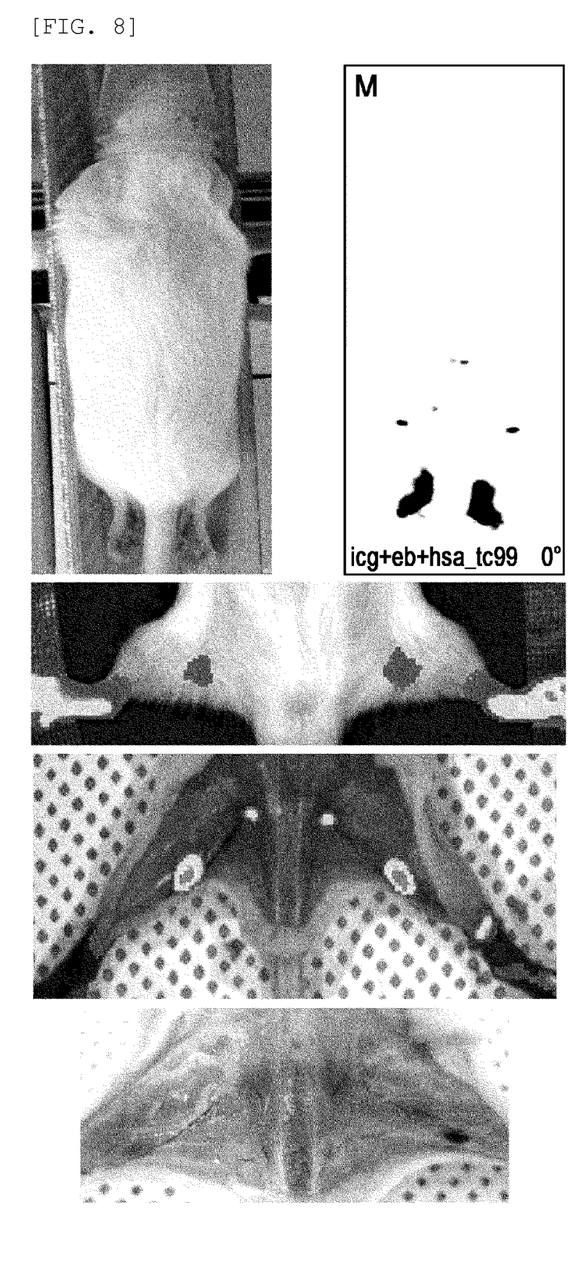
FIG. 8 shows multimode images of white mice, obtained by using [Tc-99m]Tc-indocyanine green-Evans blue-human serum albumin. The gamma image was obtained by using a SPECT system (NanoSPECT, Bioscan) without incision of skin, and the near infrared image was obtained by using a fluorescence imaging system (IVIS Lumina, Xenogen) without incision of skin. In addition, visual observation could be performed after incision of skin.

In one Example of the present invention, the albumin labeled with the radioactive isotope and bound to the near infrared fluorescent dye and visible dye was administered to white mice, and the sentinel lymph node of the white mice was imaged by gamma imaging, near infrared region imaging and visible imaging (see FIG. 8).

The sentinel lymph node marker of the present invention remains in the sentinel lymph node for a long period of time and allows for multimode imaging of the sentinel lymph node. Thus, when the marker is used, the sentinel lymph node can be accurately identified in vivo by near infrared imaging and/or gamma imaging without incision of skin, and the location of the identified sentinel lymph node can visually identified during a surgical operation of removing the identified sentinel lymph node.

Hereinafter, the present invention is described in more detail by providing Examples as below. However, these Examples are merely meant to illustrate, but in no way to limit, the claimed invention.

Example 1: Purchase of Test Materials

The type of human serum albumin used in the present invention was SK albumin 20% (SK Chemicals, Korea), and the PD-10 column (GE) was used for purification of reaction mixture. The radioactive isotope [Tc-99m]TcO$_4^-$ used in this invention was purchased from Ultra-Technekow DTE Generator (Covidien). Instant thin layer chromatography (ITLC) that was used to identify labeling was purchased from Pall Life Science. TLC scanning was performed using AR-2000 radio-TLC Imaging Scanner (Bioscan). Also, the type of gamma counter used in a biodistribution experiment was the Wizard gamma counter (Perkin Elmer). BCA protein assay kit and Ellman's reagent were purchased from Pierce, and other reagents and solvents were purchased from Sigma-Aldrich. Gamma images of animals were obtained by using NanoSPECT (Bioscan) and near infrared region (NIR) fluorescent images were obtained by using IVIS Lumina (Xenogen).

Example 2: Preparation of Thiol Human Serum Albumin Kit

Figure 3:
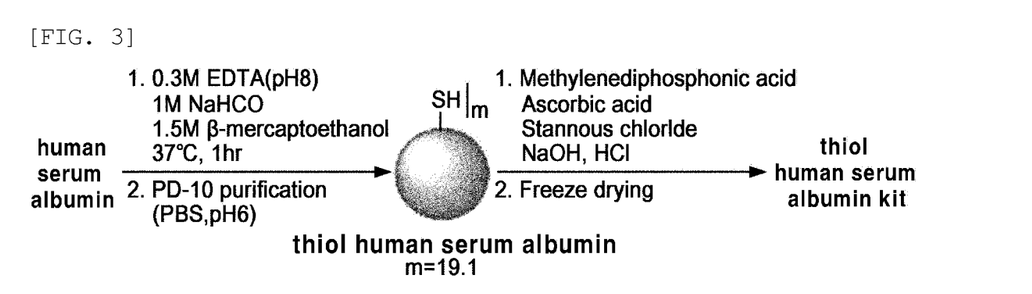
FIG. 3 shows a reaction scheme for synthesizing process of the disulfide-reduced form of albumin (thiol human serum albumin) kit.

About 40 μL of 0.3 M EDTA, 40 μL of 1 M NaHCO$_3$ and 50 μL of 1.5 M 2-mercaptoethanol were added to a solution of 0.030 mL (6 mg) of 20% human serum albumin in 1 mL of 0.1 M Na$_2$CO$_3$, and the mixture solution was stirred at 37° C. for 1 hour to reduce the disulfide bonds to thiol groups. After completion of reaction, the reaction product was purified by running it through a PD-10 column, and the resulting thiol human serum albumin was distilled under reduced pressure and diluted in 1 ml of distilled water. To the diluted solution, 0.17 mg of methylene diphosphonic acid, 3.7 μg of ascorbic acid and 8.45 μg of stannous chloride were added, and the pH of the solution was adjusted to 6 by addition of NaOH and HCl. The resulting solution was placed in a glass bottle, cooled and then freeze-dried at −80° C. for 24 hours, yielding a disposable kit (FIG. 3).

The product yield of the thiol human serum albumin kit was 91.8% as measured by BCA protein quantification. Also, the amount of thiol groups in the thiol human serum albumin was analyzed by using Ellman's reagent (sulfhydryl assay reagent). The analysis results demonstrated that 19.1 thiol groups per thiol human serum albumin molecule were produced.

Example 3: Preparation of Indocyanine Green and Evans Blue

About 0.4 mg of indocyanine green was placed in a 1.5-mL light-shielded tube and 6 mg of Evans blue was placed in a 1.5-mL light-shielded tube.

Figure 4:
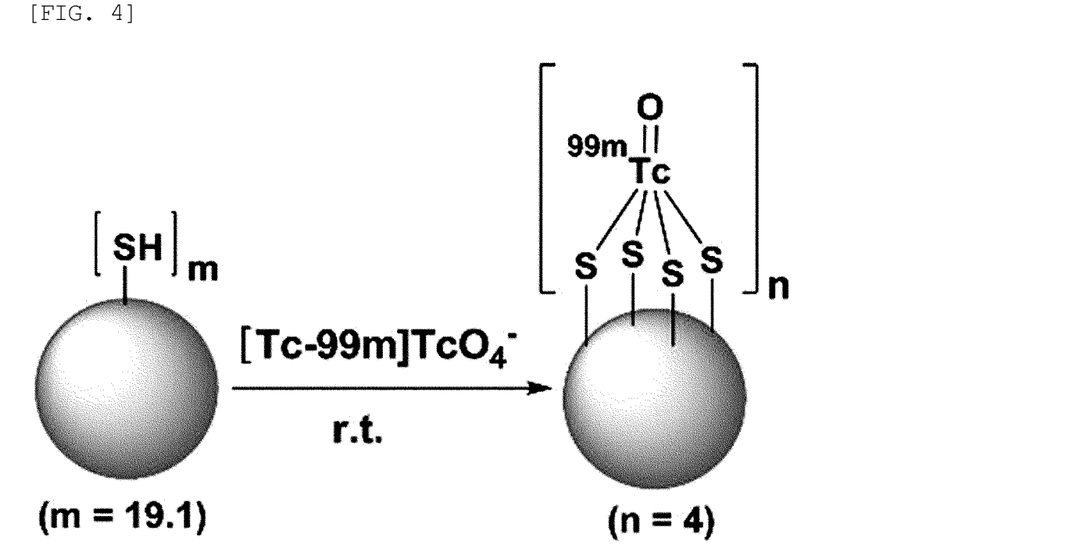
FIG. 4 shows a reaction scheme for synthesizing a [Tc-99m]Tc-labeled compound using the disulfide-reduced form of albumin.

Example 4: Preparation of [Tc-99m]Tc-Labeled Compound Using Thiol Human Serum Albumin Kit About 20 mCi/2 mL of [Tc-99m]TcO$_4^-$ was added to the thiol human serum albumin kit that was prepared in Example 2, and the mixture was left to react at room temperature for 10 minutes (FIG. 4). After completion of reaction, the reaction product was passed through a 0.45 μm sterile filter, and the synthesized products were analyzed by instant thin layer chromatography (ITLC) using ethanol: 10% ammonium acetate=1:1 as a developing solvent, and the labeling ratio was found to be >99% (FIG. 5).

Figure 6:
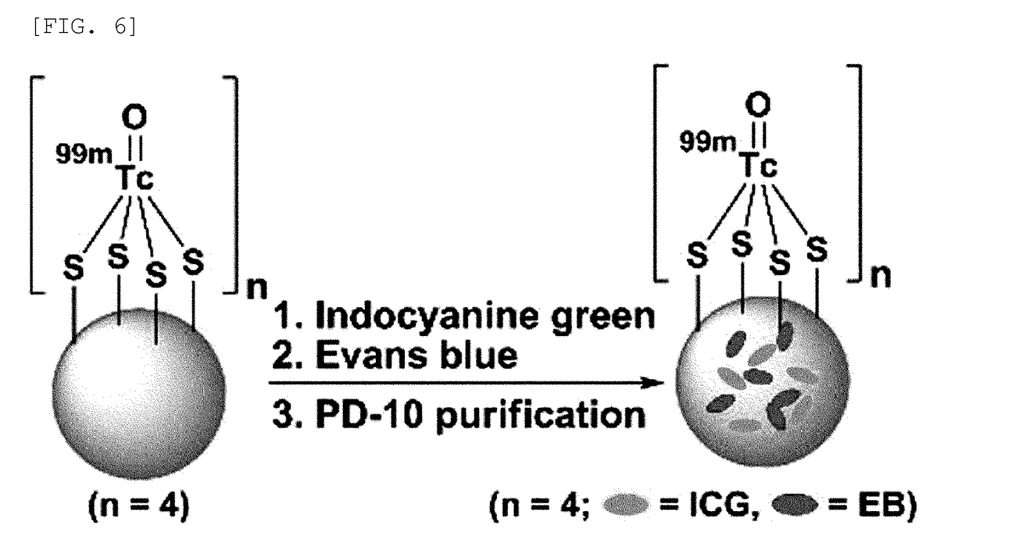
FIG. 6 is a reaction scheme for binding indocyanine green and Evans blue to [Tc-99m]Tc-human serum albumin by adsorption.

Example 5: Preparation of [Tc-99m]Tc-Indocyanine Green-Evans Blue-Human Serum Albumin The [Tc-99m]Tc-human serum albumin prepared in Example 4 was added to the indocyanine green tube and shaken at room temperature for 30 minutes under light-shielded conditions to induce binding of indocyanine green to the albumin by adsorption. Likewise, the resulting [Tc-99m]Tc-indocyanine green-human serum albumin was placed in the Evans blue tube and shaken at room temperature for 1 hours under light-shielded conditions. After completion of the adsorption coupling reaction, the reaction product was purified by using PD-10, yielding [Tc-99m]Tc-indocyanine green-Evans blue-human serum albumin (FIG. 6).

Figure 7:
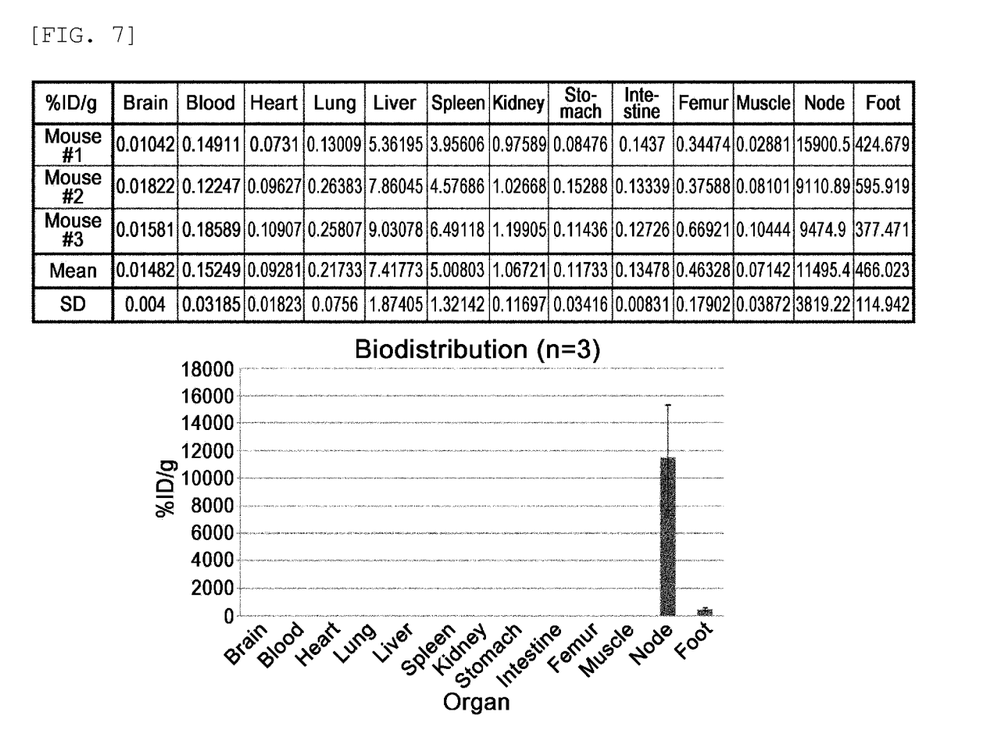
FIG. 7 shows the results of a biodistribution experiment conducted to examine the lymph node uptake of [Tc-99m]Tc-indocyanine green-Evans blue-human serum albumin.

Example 6: Biodistribution Experiment on Lymph Node Uptake of [Tc-99m]Tc-Indocyanine Green-Evans Blue-Human Serum Albumin Through performing a biodistribution experiment, the lymph node uptake of the inventive [Tc-99m]Tc-indocyanine green-Evans blue-human serum albumin was analyzed (FIG. 7). First, the foot fad of each of three white mice was injected with 80 uCi/50 uL of [Tc-99m]Tc-indocyanine green-Evans blue-human serum albumin, and after 60 minutes of injection, the mice were sacrificed, each organ was isolated from the animals, and the radioactivity of each tissue was measured using a gamma counter (Wizard gamma counter, Perkin Elmer). The biodistribution of radioactivity was determined using a standard method of calculating percentages relative to the injection amount (g). FIG. 7 shows the percentage of reactivity in each tissue. In FIG. 7, the foot is the injected area, and the node is a sentinel lymph node. As shown in FIG. 7, the uptake level of [Tc-99m]Tc-indocyanine green-Evans blue-human serum albumin was significantly higher in the sentinel lymph node than in other organs.

Example 7: In Vivo Multimode Imaging of [Tc-99m]Tc-Indocyanine Green-Evans Blue-Human Serum Albumin Using Imaging Systems In vivo multimode imaging was conducted using the inventive [Tc-99m]Tc-indocyanine green-Evans blue-human serum albumin (FIG. 8). First, gamma imaging of white mice was obtained using an animal SPECT system (NanoSPECT, Bioscan). In this experiment, the foot pad of each mouse was injected with 100 uCi of [Tc-99m]Tc-indocyanine green-Evans blue-human serum albumin, and after 60 minutes of injection, SPECT images of the mice were taken. The results demonstrated that only the injected area and the lymph node had a strong uptake of the marker, while other organs did not show any uptake of the marker. In addition, near infrared region (NIR) imaging that utilized the marker bound to indocyanine green was taken by using IVIS Lumina (Xenogen). The results shown in these images were consistent with those of gamma images and visible images which were visualized by the marker bound to Evans blue. The present multimode marker is safe for clinical use since it is derived from human serum albumin which is safe to human and bound to indocyanine green and Evans blue which are not toxic for use in human body as well. Furthermore, as the marker can remain in the sentinel lymph node for at least 1 hour, it demonstrates a high detectability of the sentinel lymph node. Also, since it is a multimode marker generating multimode signals, it provides a high accuracy in a sentinel lymph node biopsy.

What is claimed is:

1. A method for identifying a location of a sentinel lymph node without incision of skin and incising only a skin area around the sentinel lymph node and removing the sentinel lymph node through naked eye visible imaging, which comprises the following steps:
   a) administering into an animal or a human a sentinel lymph node marker for multimode imaging comprising a human serum albumin, Tc-99m, indocyanine green, and Evans blue, wherein the human serum albumin is labeled with the Tc-99m and the indocyanine green and the Evans blue are bound to the human serum albumin by adsorption, wherein the human serum albumin comprises thiol groups generated by reduction of disulfide bonds and the Tc-99m forms a coordinate bond with the thiol groups;
   b) identifying the location of the sentinel lymph node through gamma imaging of the sentinel lymph node without incision of skin and before an operation of removing the sentinel lymph node;
   c) identifying the location of the sentinel lymph node through near infrared imaging without incision of skin;
   d) incising only the skin area around the sentinel lymph node, the location of which is identified in steps b) and c), during the operation of removing the sentinel lymph node; and
   e) removing the sentinel lymph node identified from the incision site through naked-eye visible imaging without a fluorometric detection system.

2. The method according to claim 1, wherein the step a) is conducted at a single time in the method prior to the step b).

* * * * *